United States Patent [19]

Rubin

[11] 4,337,760
[45] Jul. 6, 1982

[54] METHOD FOR THE TREATMENT OF TUMORS WITH β-GLUCURONIDASE ACTIVITY DEPENDENT PHARMACEUTICALS

[75] Inventor: David Rubin, c/o Israel Medical Research Foundation, P.O. Box 3592, Jerusalem, Israel

[73] Assignees: Adolf Schwimmer, Savyon; Irwin Steven Schwartz, Tel-Aviv; David Rubin, Jerusalem, all of Israel

[21] Appl. No.: 89,888

[22] Filed: Oct. 31, 1979

Related U.S. Application Data

[63] Continuation-in-part of Ser. No. 951,269, Oct. 13, 1978, Ser. No. 951,270, Oct. 13, 1978, and Ser. No. 11,619, Feb. 12, 1979.

[51] Int. Cl.$^3$ ............................................. A61B 19/00
[52] U.S. Cl. ..................................... 128/1 R; 128/804
[58] Field of Search ................ 128/1 R, 804; 424/127

[56] References Cited

U.S. PATENT DOCUMENTS 4,106,488  8/1978  Gordon ............................. 128/1 R
4,181,132  1/1980  Parks ................................ 128/1 R

OTHER PUBLICATIONS

"Laetrille", *Merck Index* 9th Ed.

*Primary Examiner*—Henry J. Recla
*Assistant Examiner*—T. J. Wallen
*Attorney, Agent, or Firm*—Browdy and Neimark

[57] ABSTRACT

Hyperacidified tumors having high β-glucuronidase activity can be treated with glucuronides with aglycones toxic to the tumor cells with great safety toward the rest of the body by first administering an alkalinizing agent in an amount sufficient to maintain the pH level of non-tumor tissues at approximately 7.4 during the glucuronide treatment. This will cause inactivation of β-glucuronidase activity in the rest of the body. When nitrile-containing aglycones are used sodium thiosulfate is also administered to avoid cyanide poisoning. Novel glucuronides are disclosed the aglycones of which exert a higher toxic effect in an acid environment or are water-soluble only in an alkaline environment. Such compounds have particular utility with the above process. By substituting radioisotopes into the aglycone, diagnosis and in situ radiation therapy may be accomplished. Bacterial cells having β-glucuronidase activity may also be diagnosed and treated in accordance with the present invention. A urine test is disclosed to determine the amount of free glucuronic acid in the urine which is an indication of the presence of a tumor in the body having high β-glucuronidase activity. Novel methods of synthesizing the glucuronide used in the present invention are also disclosed.

10 Claims, No Drawings

METHOD FOR THE TREATMENT OF TUMORS WITH β-GLUCURONIDASE ACTIVITY DEPENDENT PHARMACEUTICALS

CROSS REFERENCE TO RELATED APPLICATIONS

The present application is a continuation-in-part of U.S. application Ser. No. 951,269 filed Oct. 13, 1978, U.S. application Ser. No. 951,270 filed Oct. 13, 1978, and U.S. application Ser. No. 11,619 filed Feb. 12, 1979, the entire contents of all of which are hereby incorporated by reference.

TECHNICAL FIELD

The present invention relates to the treatment of tumors exhibiting β-glucuronidase activity by means of glucuronides having toxic aglycones and, more particularly, to an improvement of such processes which eliminates damage to the kidneys. The toxic aglycones may incorporate a nitrile group. The invention further relates to the treatment of certain bacterial infections having β-glucuronidase activity. The present invention further relates to a new class of glucuronides whose aglycone's activity or water solubility is pH dependent as well as the method of preparation of such glucuronides. The present invention still further relates to a novel nitrile-containing glucuronide. Finally, the present invention also relates to a diagnostic urinalysis test by which the presence of tumors having β-glucuronidase activity can be determined.

BACKGROUND ART

There have been many reports in the prior art relating to the general concept of providing direct transport of an agent which is toxic to tumor cells directly to tumors having β-glucuronidase activity by conjugating the agent with glucuronic acid. Among such reports are Von Ardenne, M. et al. Agressologie, 1976, 17, 5, 261–264; East German Pat. No. 122,386; German Offenlegungschrift 22 12 014; Sweeney et al, Cancer Research, 31, 477–478, Apr. 1971; Baba et al, Gann, 69, 283–284, 1978; and Ball, C. R., Biochem. Pharm., 23, 3171–3177 (1974).

The Von Ardenne reference suggests broadly many types of aglycones which may be conjugated to glucuronic acid and will be active at the tumor site. These include, broadly, alkylating groups, antimetabolites, cytotoxins, membrane-active (lytic) groups, glycolysis stimulators, respiration inhibitors, inorganic and organic acids and cell cycle stoppers. The East German patent also suggests many such combinations including 5-fluorouracil-glucuronide, methotrexate-glucuronide, 6-mercaptopurene-glucuronide, aniline mustard-glucuronide and many others. The Offenlegungsschrift also mentions a large number of glucuronides. The Sweeney article relates to the anti-tumor activity of mycophenolic acid-β-D-glucuronides, Baba relates to the anti-tumor activity of 5-fluorouracil-O-β-D-glucuronide, and Ball relates to the anti-tumor activity of p-hydroxyaniline mustard glucuronide.

It has also been reported that the selectivity of this transport mechanism can be improved by hyperacidification of the tumor cells. The Von Ardenne reference supra, as well as the East German patent, clearly recognize the importance and the feasibility of hyperacidification of the tumor cells when using the glucuronide mechanism. Th Von Ardenne reference speaks of a method that yields a pH difference of at least 1 pH unit and may therefore by used as a basis for selectivity. It refers to reaching steady state conditions after hyperacidification in which the brain pH is 7.0 and the tumor tissue pH is approximately 5.5 to 6.0. Note also Von Ardenne, M. et al, Pharmazie, 32 (2): 74–75, 1977.

Bicker, U., Nature, 252, Dec. 20–27, 1974, pp. 726–727, particularly notes that lysosomal enzyme β-glucuronidase has an optimum pH of 5.2 and that for anti-tumor activity of glucuronides, the pH must be lowered such as by the administration of glucose. Experiments are detailed which indicate that the hyperacidification by glucose is necessary in order to obtain significant deconjugation of glucuronides.

Even with hyperacidification of the tumor cells by known methods as, for example, glucose administration, however, there is still a problem in that other organs and tissues of the body which have a naturally occurring high β-glucuronidase activity, will also release the toxic aglycones and thereby cause damage to healthy tissues. This is most particularly a problem with regard to the kidney which normally has an acid pH environment.

It has been suggested in British Pat. No. 788,855 that mandelonitrile-β-D-glucuronic acid may be used in the treatment of malignant tumors as β-glucuronidase is prevalent in malignant tissues and will selectively attack mandelonitrile-β-D-glucuronic acid at the site of the malignant tumors to split off hydrogen cyanide. U.S. Pat. No. 2,985,664 is also related to mandelonitrile-β-D-glucuronic acid and a method of producing same. These compounds have been named Laetrile by the patentees of the above-mentioned patents.

It has been discovered, however, that none of the methods of producing this compound set forth in the above-mentioned patents are reproducible. The present inventor has discovered that attempts to oxidize prunasin produce the glucuronide of mandelic acid because the CN group is unstable. Attempts to condense mandelonitrile with glucuronic acid or glucuronolactone or tetra-acetyl-glucuronolactone halogenide failed because the mandelonitrile tends to polymerize.

An article by Fenselau, C. et al in Science, 198 (4317) 625–627, 1977, entitled "Mandelonitrile β-Glucuronide: Synthesis and Characterization" confirms that the synthesis described in the original patents has not been reproduced. This article also confirms that while it was mandelonitrile-β-D-glucuronide which was originally given the name Laetrile, this compound does not appear in the Mexican preparations marketed as Laetrile. The major component of preparations currently marketed as Laetrile is amygdalin which may be easily prepared from natural source material, such as kernels of apricots, almonds, and other members of the Prunus family. However, amygdalin cannot be split by the enzyme β-glucuronidase.

The Fenselau reference teaches a method for the biosynthesis of mandelonitrile β-D-glucuronic acid. While this method may be satisfactory for producing laboratory amounts of the compound, such a biosynthetic process would no doubt be very difficult and costly to commercialize.

The problems involved in the chemical synthesis of mandelonitrile β-D-glucuronic acid also exist for the synthesis of any glucuronide the aglycone of which is a strong electron acceptor. This is because the glucuronide will become deconjugated (hydrolyzed) in the course of the classical process.

Before using glucuronide treatment, there must be a diagnosis of tumors having β-glucuronidase activity. The prior art (for example, Sweeney, supra) suggests taking a biopsy to determine such β-glucuronidase presence. It would be desirable to be able to detect the presence of such β-glucuronidase activity tumors by a simple urine test.

DISCLOSURE OF INVENTION

Accordingly, it is an object of the present invention to overcome the deficiencies of the prior art.

It is another object of the present invention to provide for the improved treatment of malignant tumors.

It is further object of the present invention to provide an improved process for the treatment of malignant tumors having high β-glucuronidase activity.

It is still another object of the present invention to provide such an improved process which is selectively toxic to tumor cells, but does not harm healthy tissue.

It is yet another object of the present invention to provide such an improved process in which the tumor cells are selectively treated with nitrile-containing compounds with concurrent therapy to avoid the possibility of cyanide poisoning in the rest of the body.

It is still another object of the present invention to provide new compounds and pharmaceutical compositions which have very low toxicity to the organism as a whole but very high selective toxicity toward tumor cells, and particularly tumor cells having high β-glucuronidase activity.

It is another object of the present invention to provide a diagnostic method using radiactive isotopes to selectively label tumor cells so that both primary tumor cells and metastases can be precisely located.

It is yet another object of the present invention to provide a process of preparing the compounds which may be used in such processes of treatment.

It is still another object of the present invention to provide a process for preparing mandelonitrile β-D-glucuronic acid by totally chemical synthesis.

It is still another object of the present invention to provide a method for testing the urine to determine the presence of tumors having β-glucuronidase activity.

It is still another object of the present invention to provide a process and compositions for the treatment of bacterial infections when the bacteria exhibit β-glucuronidase activity.

These and other objects of the present invention will be better understood from a reading of the following summary and the detailed description of the present invention.

It has now been found that the selectivity of glucuronide compounds toward tumors can be greatly increased and the possible deconjugation of the toxic aglycones in normal parts of the body can be greatly minimized by administering to the patient, prior to or simultaneously with administration of the glucuronide, an alkalinizing agent which will maintain the pH of the rest of the body at a pH of about 7.4. It is known that at a pH of 7.4 and above β-glucuronidase activity is substantially nil. Thus, the administration of alkalinizing agents such as bicarbonates or other basic salts will substantially decrease and eliminate β-glucuronidase activity which naturally occurs in certain healthy tissues such as the kidneys, spleen, and liver. Such an administration of alkalinizing agent will not diminish the acidity of the tumor cells themselves, however, in view of the naturally low pH of the tumor cells, the mechanism of prior hyperacidification, and the lack of substantial blood perfusion through the tumor areas, as well as other possible mechanisms. It has been suggested in the literature, in fact, that bicarbonate will actually increase the acidity of the cancer cells. Gullino, P.M., et al, J.N.C.I., 34, 6, 857–869 (1965).

Since the β-glucuronidase activity of the tumor cells will be enhanced by acidification, and the β-glucuronidase activity of the rest of the body, particularly of the kidneys, will be substantially eliminated by alkalinization, the toxic aglycones will only be released at the tumor site itself due to deconjugation of the glucuronides by the action of β-glucuronidase. Without the alkalinization step, substantial amounts of toxic materials may be released, for example, in the kidneys, and the toxic aglycones so released may cause substantial damage to these organs. Thus, only through the use of the present invention can glucuronides of compounds toxic to tumor cells be used clinically with a great degree of safety. The greater the toxicity of the aglycones, the more important is the alkalinization step.

A further feature of the present invention is the use of certain novel glucuronide compounds which are particularly suitable for use in the present invention because of the significant pH differential between the tumor cells and surrounding healthy tissue. If the aglycone is more active at lower pH, or non-polar in acid condition and becoming polar only in alkaline condition, i.e., the aglycone is water-soluble at pH ranges above about 7 and lipid-soluble at pH ranges below 7, then the selectivty of the present invention is further inreased. Using these new compounds, even if there is deconjugation elsewhere in the body, the aglycone will be water-soluble due to the alkaline pH and be washed out of the system quickly. However, in the low pH range of the hyperacidified tumor cells, the aglycone will actually become attached to the tumor cells and will not become solubilized and washed away. Even if some amount of aglycone becomes removed from the locus of the tumor cells, they will immediately come into an alkaline environment and thus become water soluble and be quickly swept from the body.

Among the novel glucuronides in this category are 2,4-dinitrophenol-β-D-glucuronic acid; 4-chloro-m-cresol-β-D-glucuronic acid; 4,6-dinitro-o-cresol-β-D-glucuronic acid; 4-chloro-3,5-xylanol-β-D-glucuronic acid; chlorothymol-β-D-glucuronic acid; 2-phenyl-6-chlorophenol-β-D-glucuronic acid; 5-chloro-7-iodo-8-quinolinol-β-D-glucuronic acid; and podophyllotoxin-β-D-glucuronic acid. The chloro-m-cresol-β-D-glucuronic acid is of particular interest as it actually loses its toxic activity in an alkaline environment.

Aside from the anti-tumor utility, these novel compounds, and any other glucuronide compounds having cytotoxic aglycones, also have an anti-bacterial activity, particularly against those types of bacteria having glucuronidase activity. It is known, for example, that streptococcus, staphylococcus and *E. coli* bacteria have β-glucuronidase activity. Therefore, if the glucuronides come into contact with these bacteria, they will become deconjugated and the cytotoxic aglycones will be toxic to the bacteria.

It has been reported that the optimum pH of bacterial β-glucuronidase is higher than the optimum pH of the β-glucuronidase of normal healthy internal organs, such as liver, spleen, kidney, etc. Therefore, upon alkalinization of the body in accordance with the method discussed hereinabove, the β-glucuronidase activity of the organs will be substantially eliminated, while that of the bacteria, although alkalinized, will still be present. The administered glucuronide will then only be deconjugated to its active form at the site of the infection. Since tumor cells are not being treated for this utility, no hyperacidification step is necessary.

While the glucuronide compounds discussed hereinabove are preferred for use in the process of the present invention, it should be understood that the glucuronides of any anti-tumor drug, including those previously suggested in the prior art as being useful, may be used to greater advantage in the process of the present invention since the selectivity thereof will be increased by the alkalinization step. Non-limiting examples of compounds, some of which may have been known, which may also be used in the present invention, even though they have no presently known differentiation of toxicity or solubility which is pH dependent, include 5-fluorouracil-O-β-D-glucuronic acid; p-hydroxyaniline mustard-β-D-glucuronic acid; methotrexate-β-D-glucuronic acid; floxuridine-β-D-glucuronic acid; cytarabine-β-D-glucuronic acid; melphalan-β-D-glucuronic acid; hydroxyurea-β-D-glucuronic acid; adriamycin-β-D-glucuronic acid; thiouracil-β-D-glucuronic acid; chlorophenol-β-D-glucuronic acid; methacrylonitrile-β-D-glucuronic acid; fluoroacetic acid-β-D-glucuronic acid; etc.

Other preferred forms of glucuronide for use in the present invention are ones the aglycones of which exert their toxic effect on the cancer cells at the cell membrane. The anti-tumor toxicity of many conventional anti-cancer drugs requires that they penetrate to the nucleus of the mitochondria within the cell. In prior cancer treatment chemotherapy processes the drugs had to be designed to attack only cancer cells and not all of the other cells of the body with which they come into contact. This is why particular effort have been made in the past to develop anti-neoplastic drugs which interfere with cell division. Many of these drugs must actually enter the nucleus of the cancer cell to be effective. For such drugs, therefore, one must always be concerned that they be transported without change through the membrane of the cancer cell before they can exert their toxic effects.

By means of the process of the present invention it is not important that the toxicity of the agent be directed only at cancer cells as opposed to all of the healthy cells of the human body, in view of the fact that by means of the process of the present invention the aglycone is only released at the cancer site. Accordingly, a particularly useful aglycone is one which exerts its cell toxicity by attacking the cell membrane itself. In this way one need not be concerned with the transfer mechanism of the drug through the membrane. Furthermore, by attacking the membrane the nature of the membrane is changed and the antigenic properties of the cells are changed. Therefore the immunilogical system of the host will aid the toxic agent in ridding the host of these cells. Accordingly a much lower dose need be used.

Examples of aglycones which exert this effect include phenol and cresol. Therefore particularly useful glucuronides for use in the process of the present invention include phenol-β-D-glucuronic acid and cresol-β-D-glucuronic acid.

Other steps for increasing β-glucuronidase activity at the tumor cells may also be undertaken. One method of doing this is to elevate the temperature of the toxic cells at the time of treatment. This may be done by elevating the temperature of the entire body such as by use of a pyrogenic drug or by elevating the temperature soley in the area of the toxic cells, such as by microwave radiation or electrical current. Raising of the temperature increases β-glucuronidase activity thereby increasing the efficiency of the deconjugation of the glucuronides. It is known that an elevation of temperature of 3° C. increases β-glucuronidase activity by 50%.

Known pyrogenic drugs include etiocholanolone, progesterone, dinitrophenol, dinitrocresol, etc. Both dinitrophenol and dinitrocresol are also cytotoxic, as will be discussed hereinbelow. Therefore the use of these compounds are preferred, especially when administered as the glucuronide. This gives the result that when the glucuronide is deconjugated at the tumor site the aglycone will act not only to denature the cytoplasmic protein but also to raise the temmperature directly in the region of the tumor cells thus greatly increasing the efficiency of further deconjugation.

Local hyperthermia in the region of suspected tumor cells is preferred to general hyperthermia because general hyperthermia will also increase the β-glucuronidase activity in healthy cells. However, because of the alkalinization step this is not a major problem. If the hyperthermia is local, then this provides an additional degree of certainty that the glucuronides will only become deconjugated at the tumor site. The application of microwave treatment directed at the suspected tumor site is one way to achieve total hyperthermia. Due to the different electrical resistence of tumor cells, another method of achieving some degree of local hyperthermia is by administering a low electrical current through the body.

A further manner of increasing β-glucurondase activity selectively at tumor cells is by administration of estrogen to female patients or testosterone to male patients. It has been reported that these compounds induce β-glucuronidase activity in trophoblastic cells. Certain tumor cells are known to be trophoblastic; this method would thus be particularly useful for those cells. The alkalinization step would prevent damage to healthy trophoblastic cells.

Another feature of the present invention relates to the process of preparing the glucuronides. It has been discovered that it is impossible to prepare conjugates of glucuronic acid by the classical methods when the aglycone is a strong electron acceptor, as these compounds must first be prepared as the methyl ester of the glucuronic acid and it is not possible by the classical methods to convert the methyl ester to the acid without deconjugating the aglycone. While barium methoxide has been suggested for this purpose in a related process in U.S. Pat. No. 2,985,664, it has been discovered that barium methoxide will not work. However, it has now been discovered that if barium hydroxide is used, the methyl ester of the aglycone of the glucuronide may be converted to the barium salt, and the barium salt may be converted to the free acid by the use of sulfuric acid without deconjugation of the glucuronide. Moreover, removal of the acetyl protecting groups is accomplished in the same step, thus eliminating the need of a separate step to accomplish this function.

This novel step using barium hydroxide may also be used in the chemical synthesis of mandelonitrile β-D-glucuronic acid. However, this process will fail when attempting to synthesize mandelonitrile β-D-glucuronic acid because when attempting to condense the methyl(-tri-O-acetyl α-D-glucopyranosyl)halide-uronate with mandelonitrile, the mandelonitrile will tend to polymerize rather than to create the hemi-acetal bond with the glucuronic acid.

The method of synthesis of mandelonitrile β-D-glucuronic acid in accordance with the present invention comprises first converting mandelic acid to mandelic amide by reaction with gaseous ammonia. The mandelic amide is then reacted with the methyl(tri-O-acetyl β-D-glucopyranosyl)bromide-uronate to produce the methyl ester of the mandelic amide triacetyl glucuronic acid. This compound may then be mixed with acetic anhydride to convert the mandelic amide to mandelonitrile. Treatment with barium hydroxide and sulfuric acid will produce the mandelonitrile β-D-glucuronic acid.

Another feature of the present invention resides in an additional safety feature by which the healthy tissues of the body are protected against possible release of hydrogen cyanide from nitrile-containing aglycones. This feature is preferably in addition to the feature disclosed hereinabove with respect to pH adjustment. Even with such protection against deconjugation of the glucuronide at areas of the body other than tumors, concern has been expressed about possible cyanide poisoning when using nitrile-containing glucuronides. For example, in Schmidt, E. S., et al. *J.A.M.A.* 239 (10): 943–7, Mar. 6, 1978, it was predicted that there will be an increased incidence of cyanide poisoning in man as Laetrile (amygdalin) becomes more readily available. It is not known whether it is the entire nitrile-containing aglycone, mandelonitrile, which exerts the toxic effect on the tumor cells, or whether it is the hydrogen cyanide which is released upon the decomposition of mandelonitrile. It is theorized, however, that it is the entire nitrile-containing aglycone which exerts the toxic effect on the tumor cells. Therefore, it is important to protect the rest of the body against possible release of hydrogen cyanide from the nitrile-containing aglycones. This is accomplished in accordance with the present invention by the concurrent administration of sodium thiosulfate when glucuronides of nitrile-containing aglycones are used. It is well known that sodium thiosulfate is an antidote for cyanide poisoning. Sodium thiosulfate in the presence of the enzyme rhodanase converts hydrogen cyanide to sodium thiocyanate.

It is believed that the concurrent administration of sodium-thiosulfate will not affect the toxicity of the aglycone at the cancer site for two reasons. First, even in the presence of rhodanase, sodium thiosulfate will not affect the mandelonitrile molecule itself. Therefore, if it is the entire mandelonitrile molecule which is toxic to the cancer cells, then the presence of sodium thiosulfate will not affect this toxicity. Furthermore, even if it is the hydrogen cyanide which is toxic to the cancer cells when released at the site of the cancer cells, it has been suggested in the literature that cancer cells do not contain rhodanase. See Lupo, M. et al, "Critical Review of Studies on Malignant Diseases," Minerva Med. 67 (30) 1973–1981, 1976. Therefore, the concurrent administration of sodium thiosulfate will protect normal cells against cyanide poisoning but will not affect the attack of the cyanide on the tumor cells.

In view of the relative lack of toxicity of glucuronide compounds, and in view of the mechanism of the present invention by which the toxic aglycone is released only at the tumor site, and further in view of the protection of the present invention against possible hydrogen cyanide release at other parts of the body, it is entirely possible to use glucuronides of other toxic nitrile-containing aglycones in the process of the present invention. One such compound is methacrylonitrile β-D-glucuronic acid.

Because of the acid-alkaline differentiation between the tumor cells and the rest of the body achievable by the process of the present invention, it is possible to use certain compounds which denature cytoplasmic proteins or affect the energy supply of the cells directly, without first conjugating with the glucuronic acid. This can only be done, however, if the compound is one whose activity or solubility is pH-dependent. Examples of such compounds are 2,4-dinitro-phenol; chloro-m-cresol; 4,6-dinitro-o-cresol; 4-chloro-3,5-xylanol; chlorothymol; 2-phenyl-6-chlorophenol; 5-chloro-7-iodo-8-quinolinol; and podophyllotoxin. The use of these compounds directly without first conjugating with glucuronic acid would be particularly useful in treating tumors with no demonstrated β-glucuronidase activity.

Another feature of the present invention is related to the extremely high tumor selectivity which is achievable in accordance with the present invention. In view of the selectivity, if one or more of the atoms of the aglycone is exchanged with a radioactive isotope, a local radioactivity can be exerted. This method is not only important for diagnostic purposes to trace the tumor and its metastases, but if an isotope is chosen with β-radiation activity, then this method may also be used for local radiation treatment at the cancer site. This use of radioactive isotopes is particularly important when using an aglycone which is known to be non-polar in acid condition and polar in alkaline condition. When this quality exists, the aglycone is accumulated at the cancer site not only because of the β-glucuronidase activity, but also because of its insolubility in water at the cancer site. At the same time, the compounds with the radioactive isotopes are washed away from the rest of the body. The use of p-iodophenol β-D-glucuronic acid produces an aglycone, p-iodophenol, which fulfils these demands. A radioactive isotope of iodine can be used as the iodine constituent of this compound. It is preferable to use $^{131}$I for labelling and $^{133}$I for treatment, as the former is richer is gamma radiation while the latter is richer in beta radiation. In order to prevent the iodine from migrating to the thyroid gland, premedication with non-radioactive Lugol's solution may be used for saturating the thyroid gland.

Another compound which can be easily radioactive labelled is the glucuronide of phenylsulfazole. A radioactive sulfur atom can be used. This compound does not migrate to the thyroid gland, and the aglycone is not soluble in water.

Before treatment of patients in accordance with the present invention, it should be ascertained that the particular type of tumor involved has high β-glucuronidase activity. This may be done in a number of ways. One way is to assay tumor cells obtained in a biopsy for β-glucuronidase activity. If such a test is positive, then the pharmaceutical compositions of the present invention may be administered.

A second method is the administration of a glucuronide whose aglycone has been labelled with a radioactive isotope. If upon a full body scan it is found that the radioisotope is accumulated at any specific areas of the body, then this will indicate not only the location of the tumor but the fact that the tumor has sufficient β- glucuronidase activity to deconjugate the glucuronide. After this has been determined, the appropriate amount of the glucuronide of choice may be administered. If there are no tumors present, or if the tumors are of the type which do not have β-glucuronidase activity, then there will be no accumulation of radioisotope in the body as the alkalinization step of the present invention eliminates all usual β-glucuronidase activity and the isotope will be passed through the body.

Another method of diagnosing tumors which are treatable by means of the present invention is to test for the presence of free glucuronic acid in the urine. While the presence of glucuronides in the urine is common, the presence of free glucuronic acid in the urine, and particularly the presence of increasing amounts of glucuronic acid when tested over a period of several days, is a potent indication of the presence of tumors with β-glucuronidase activity. It is hypothesized that the presence of free glucuronic acid in the urine in cancer patients is caused by the action of β-glucuronidase in the cancer cells on the intercellular filaments and connective tissue. Glucuronic acid is a reaction product of such activity because the intercellular filaments and connective tissue are composed of polymers of which glucuronic acid is an element and which are known substrates for the enzyme β-glucuronidase.

A method of distinguishing free glucuronic acid from conjugated glucuronides in the urine is another feature of the present invention. Both glucuronides and glucuronic acid give a chromogenic complex with tetraborate in concentrated sulfuric acid which reacts with m-hydroxydiphenyl to create a colored water-soluble complex. When lead acetate is added at an alkaline pH, the glucuronides precipitate and the addition of ditizone (dithiosemicarbizone) makes a stable complex with the excess lead. Accordingly, an optical reading may be taken representative of the amounts of total glucuronides and free glucuronic acid after tetraborate and m-hydroxydiphenyl have been added. A second reading may then be taken after the conjugated glucuronides and excess lead have been removed from the aqueous phase by the addition of basic lead acetate and after ditizone has been added. Alternatively, the conjugated glucuronides can be removed by reaction with barium hydroxide. The addition of barium hydroxide to the urine sample will cause precipitation of the conjugated glucuronides but not of the free glucuronic acid. After centrifugation and filtration the conjugated glucuronides are eliminated and what remains is only the free glucuronic acid. A reading representative of the amount of free glucuronic acid may then be taken. This alternative procedure bypasses the necessity of the use of ditizone.

BEST MODE FOR CARRYING OUT THE INVENTION

While many glucuronide compounds having aglycones which are toxic to cancer cells have been described theoretically in the literature, very few have actually been produced. This is because they are very difficult to synthesize, particularly when the aglycone is a strong electron acceptor. The improved method of the present invention avoids the problem and permits the production of conjugates of glucuronic acid of almost any type of aglycone. The standard methods can be used to form the methyl ester of the triacetyl glucuronic acid conjugates but it is often quite difficult to go from the triacetyl methyl ester to the glucuronic acid conjugate. This problem has been solved by treatment in accordance with the process of the present invention.

The glucuronides in accordance with the present invention and for use in the process of the present invention, may be synthesized from methyl(tri-O-acetyl-β-D-gluco-pyranosyl bromide)-uronate which is the active glucuronic acid and is formed in accordance with the teachings of Bollenback, G. N., et al, J. Am. Chem. Soc. 77, 3310, (1955). This compound is condensed with the aglycone in a solution of quinoline, phenol, methyl cyanide or methyl nitrite catalyzed by silver oxide or silver carbonate. Another method of condensation is to use sodium or potassium hydroxide as the condensing agent in aqueous acetone solution. The reaction scheme is illustrated as follows:

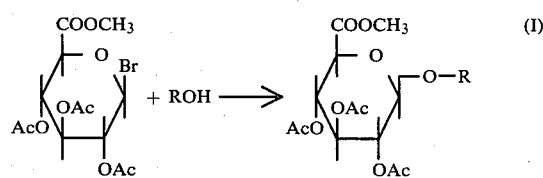

wherein ROH is the desired aglycone.

If the methyl ester of the glucuronide is desired, the protecting acetic acid groups may be removed by anhydrous sodium methoxide or anhydrous barium methoxide in accordance with the following reaction:

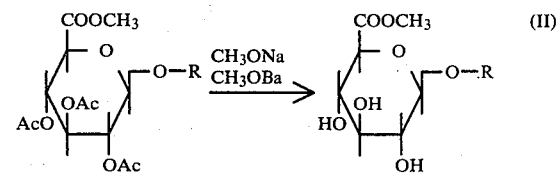

The acid may be produced by reacting the triacetyl methyl ester with barium hydroxide to produce the barium salt in accordance with the following reaction:

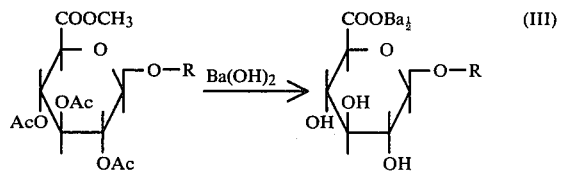

This barium salt of the glucuronide precipitates. An equimolar solution of sulfuric acid releases the free glucuronide according to the following reaction:

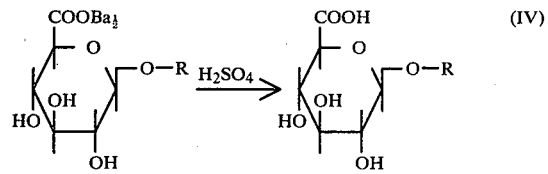

Example I shows the preparation of 2,4-dinitrophenol-β-D-glucuronic acid.

EXAMPLE I

Synthesis of 2,4-Dinitrophenol-β-D-glucuronic Acid

Methyl-(2,3,4-tri-O-acetyl-β-D-glucopyranosyl bromide)-uronate was prepared in accordance with the process of Bollenback, G. N., et al, *J. Am. Chem. Soc.* 77, 3310 (1955). Four grams of methyl(tri-O-acetyl-β-D-glucopyranosyl bromide)-uronate in acetone (80 ml) and 8.9 g 2,4-dinitrophenol were treated with 5 N potassium hydroxide (9 ml) and the solution kept at 25° C. for 24 hours, then diluted with 3 volumes chloroform. The chloroform-acetone layer was washed with water and dried. Removal of the solvent and two recrystallizations from acetone yielded the methyl-2,3,4-tri-O-acetyl-β-D-glucopyranosyl uronate of 2,4-dinitrophenol.

The free acid form of the compound was formed by treating the 2,4-dinitrophenyl-methyl(tri-O-acetyl-β-D-glucopyranosyl bromide)-uronate with a one-half molar amount of barium hydroxide to produce the barium salt. This barium salt of the glucuronide precipitates as a white amorphous material. An equimolar solution of $H_2SO_4$ releases the free glucuronide. Distillation of the supernatant yielded bright yellow-brown crystals having a melting point of 179°–180° C. This compound was incubated with β-glucuronidase and produced 2,4-dinitrophenol, thus confirming that the final product is indeed 2,4-dinitrophenol-β-D-glucuronic acid.

The other glucuronides in accordance with the present invention, e.g. chloro-m-cresol-β-D-glucuronic acid; 4,6-dinitro-o-cresol-β-D-glucuronic acid; 4-chloro-3,5,-xylanol-β-D-glucuronic acid; chlorothymol-β-D-glucuronic acid; 2-phenyl-6-chlorophenol-β-D-glucuronic acid; 5-chloro-7-iodo-8-quinolinol-β-D-glucuronic acid; and podophyllotoxin-β-D-glucuronic acid, as well as p-iodophenol-β-D-glucuronic acid and phenylsulfazole-β-D-glucuronic acid, may be made in a similar manner by reacting a stoichiometric excess of the aglycone with the methyl-(tri-O-acetyl-α-D-glucopyranosyl bromide)-uronate in 5 normal potassium hydroxide and maintaining the reaction solution at room temperature for 24 hours. The solution is then diluted with 3 volumes chloroform and the chloroform-acetone layer washed with water and dried. After removal of the solvent, the crystals which are obtained are treated with a one half molar amount of barium hydroxide to produce the barium salt which is then treated with an equimolar solution of sulfuric acid to produce the free glucuronide.

The free acid form of the glucuronide, or a salt thereof which will ionize at the conditions of use, is the preferred form of the compounds to be used in accordance with the present invention. However, pharmaceutically acceptable esters may also be used, although in most cases it would be expected that their activity would be somewhat lower due to their relatively lower affinity to β-glucuronidase. This is particularly true with respect to aglycones which are strong electron acceptors. Accordingly, whenever the term "glucuronide compound" is used in the present specification and claims it is understood to include not only the free glucuronic acid form of the conjugate but also pharmaceutically acceptable salts and esters thereof as discussed hereinabove, both in this and subsequent examples.

EXAMPLE II

Synthesis of Mandelonitrile β-D-glucuronic Acid

Mandelonitrile β-D-glucuronic acid may be synthesized, in accordance with the present invention, from methyl(tri-O-acetyl-α-D-glucopyranosyl bromide)-uronate, which is the active form of glucuronic acid, and may be produced in accordance with the teachings of Bollenback, G. N., et al, *J. Am. Chem. Soc.* 77, 3310, (1955). Since this compound cannot be directly conjugated with mandelonitrile, mandelic amide is first formed. This compound is formed by bubbling gaseous $NH_3$ into mandelic acid at 0° C. as illustrated in reaction:

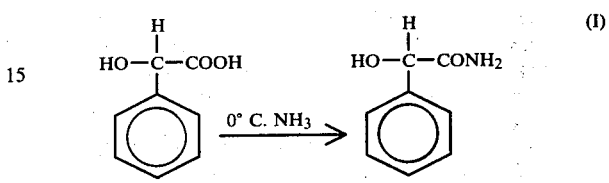

The mandelic amide is introduced to the methyl (tri-O-acetyl α-D-glucopyranosyl) bromide uronate in a solution of phenol catalyzed by a small catalytic amount of silver oxide. Besides phenol, there may be used, as solvent, quinoline, methyl nitrile or methyl cyanide. Silver carbonate may also be used as the catalyst. Another method of condensation is to use sodium or potassium hydroxide as the condensing agent in aqueous acetone solution. A stoichiometric excess of mandelic amide is preferably used. The reaction solution is maintained at room temperature for 24 hours or until the reaction is complete. The reaction is illustrated as follows:

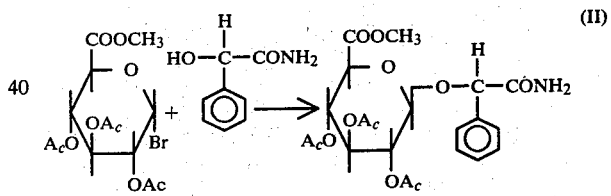

The above solution is then mixed with acetic anhydride in 1:1 molar ratio and heated to 70° C. for 30 minutes in order to convert the mandelic amide to the mandelonitrile in accordance with the following reaction:

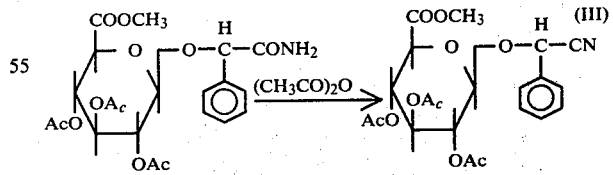

The acid is produced by reaction of the triacetyl methyl ester obtained by reaction (III) with a ½ molar amount of 0.5 N barium hydroxide which is added slowly to this solution to form a white precipitate. Preferably an excess of barium hydroxide is added until there is no more precipitation. The reaction can be illustrated as follows:

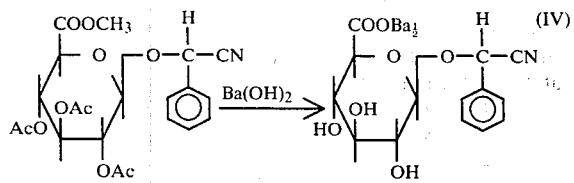

The addition of 0.5 N sulfuric acid, volume to volume, then cooling in ice water for 20 minutes, relases the free glucuronides according to the following reaction:

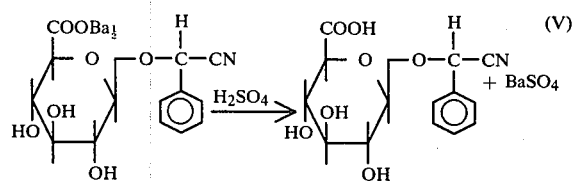

The mixture is then filtered and the supernatant is dried in vacuum and crystallized from ether.

EXAMPLE III

Synthesis of Methacrylonitrile β-D-Glucuronic Acid

Methacrylonitrile β-D-glucuronic acid or other glucuronides of nitrile-containing cytotoxic compounds may be produced in accordance with the present invention in a manner similar to that disclosed in Example II though the step of converting the methacrylonitrile to methacrylamide prior to condensation with methyl(tri-O-acetyl-α-D-glucopyranosyl bromide)-uronate will not be necessary as there is not the same polymerization problem with methacrylonitrile as there is with mandelonitrile. In general, the preferred process when condensing the aglycone directly, is to react the stoichiometric excess of the aglycone (methacrylonitrile in the case of methacrylonitrile β-D-glucuronic acid) with the methyl (tri-O-acetyl-α-D-glucopyranosyl bromide)-uronate in 5 N potassium hydroxide and maintaining the reaction solution at room temperature for 24 hours. The solution is then diluted with 3 volumes chloroform and the chloroform-acetone layer washed with water and dried. After removal of the solvent, the crystals which are obtained are treated with a one half molar amount of barium hydroxide to produce the barium salt which is then treated with an equimolar solution of sulfuric acid to produce the free glucuronide.

EXAMPLE IV

Acute Intravenous Toxocity to Rabbits of Mandelonitrile β-D-Glucuronic Acid

NZW rabbits in the weight range of 2,000 to 3,200 g for females and 2,200 to 3,800 g for males were injected intravenously with mandelonitrile β-D-glucuronic acid solution. Rabbits injected with saline alone served as the control. The mandelonitrile β-D-glucuronic acid solution contained 10% mandelonitrile.

During the 14 day observation period a record was kept of all mortalities and signs of toxicity. Table I gives the range finding screen.

TABLE I

Mortality Data for Groups of Rabbits (2 per Group) Intravenously injected with DMBG Solution.

Range Finding Screen

| Dosage ml/kg | Mortality Ratio no. of deaths/ no. dosed |
|---|---|
| 0.25 | 0/2 |
| 0.5 | 1/2 |
| 1.0 | 2/2 |
| 2.0 | 2/2 |
| 4.0 | 2/2 |

The results of the preliminary range finding tests as shown in Table I indicated that the median lethal intravenous dose (LD-50) was in the region of 0.23–2 ml per kg body weight.

Dosing was then extended to larger groups of rabbits (5 males and 5 females per group) in order to locate the median lethal dose more precisely. Table II gives mortality data for this larger group.

TABLE II

Mortality Ratio of Rabbits Intravenously Injected with DMBG Solution. Full Scale Test - Weight range: Females 2,000–3,200 g, Males 2,200–3,800 g.

| | Dosage ml/kg | Mortality ratio No. of deaths/ No. dosed | Time of death after dosing No. of animals | No of hours |
|---|---|---|---|---|
| Males | 0.44 | 0/5 | — | — |
| | 0.66 | 2/5 | 2 | <3 |
| | 1.0 | 3/5 | 3 | <3 |
| | 1.5 | 4/5 | 4 | <3 |
| | 2.25 | 5/5 | 5 | <3 |
| Females | 0.44 | 0/5 | — | — |
| | 0.66 | 2/5 | 2 | <3 |
| | 1.0 | 5/5 | 5 | <3 |
| | 1.5 | 5/5 | 5 | <3 |
| | 2.25 | 5/5 | 5 | <3 |

Signs of reaction to treatment, observed 2 minutes after dosing, included ataxia and paralysis. Two minutes later a few animals of the high dose group died. All the deaths of all the groups occurred within 3 hours after dosing. The animals which survived did not show any clinical symptoms during the following 14 days. Autopsy of all animals did not show clear gross pathological changes.

The acute median lethal intravenous dose (LD 50) and its 95% confidence liminits calculated by the method of Weil, C. S., 1952, *Biometrics,* 8:249, to rabbits of mandelonitrile-β-D-glucuronic acid 10% solution are calculated to be:

Males: 0.84187 (0.78087–0.90287) ml/kg body weight
Females: 0.6873 (0.64417–0.73043) ml/kg body weight From the above data, it is believed that the maximum safe dose is on the order of 0.44 ml/kg body weight, and it is believed that this limit should not be exceeded in human therapy.

Prior to therapeutic treatment with compounds of the present invention, the presence of tumor having high β-glucuronidase activity must be diagnosed. The most positive way to definitively ascertain whether a tumor is present having high β-glucuronidase activity is to conduct a biopsy and to assay the tumor cells obtained for β-glucuronidase activity. This, of course, is not feasible for most kinds of tumor. Another way to diagnose for the presence of tumors having β-glucuronidase activity, is to conduct a urine test in order to determine the presence of free glucuronic acid. Normal patients show between 200 to 400 mg per 24 hours of free glucuronic acid in the urine. Cancer patients with well developed tumors which have β-glucuronidase activity will show greater than 2,000 to 7,000 mg per 24 hours free glucuronic acid. Accordingly, using the test of the present invention, if substantially more than 400 mg per 24 hours of free glucuronic acid is shown, then this is an excellent indication of the presence of tumors having high β-glucuronidase activity.

A negative indication on this urine test will not conclusively rule out the presence of tumors having β-glucuronidase activity, because tumors in their initial stages, though they might have β-glucuronidase activity, might not release sufficient free glucuronic acid to cause a positive reading of the urine. Therefore, the urine test should be repeated, and if an increasing amount of free glucuronic acid is found, then this is another indication of the presence of a tumor having β-glucuronidase activity. An example of the method of determining the amount of free glucuronic acid in the urine is given in Example V.

EXAMPLE V

Test for Glucuronic Acid in Urine

Both glucuronides and glucuronic acid give a chromogenic complex with tetraborate and concentrated sulfuric acid which reacts with m-hydroxydiphenyl to create a colored water-soluble complex. Furthermore, glucuronides precipitate with basic lead acetate when pH is 8, while the free glucuronic acid is not affected by the lead acetate. Complexing the excess lead with dithiocarbizone forms a stable complex with lead which can be removed, thus leaving free glucuronic acid.

To 10 cc of a urine sample 0.1 N ammonium hydroxide is added until a pH of 8 is reached. An excess of saturated solution of basic lead acetate is then added causing precipitation of the conjugated glucuronides. The sample is then centrifuged and the supernatent separated. Two cc of the supernatant is then treated with 10 cc of 10% dithiocarbizone (ditizone) in chloroform in order to remove the excess lead. After waiting until the separation is complete, the aqueous phase is separated. To 0.2 cc of the aqueous phase is added 1.2 cc of sodium tetraborate in concentrated $H_2SO_4$. The mixture is mixed well in a test tube and chilled in crushed ice. The test tube is then heated for 5 minutes in boiling water and immediately cooled in ice until it becomes cold. Twenty microliters of 0.15% m-hydroxydiphenyl in 0.5% NaOH is then added. After waiting 5 minutes, the optical density is read at a wavelength of 5200 Å. The reading obtained represents the amount of free glucuronic acid present in the urine.

The total amount of free and conjugated glucuronic acid is simply determined by directly treating the sample with tetraborate and hydroxydiphenyl, without first removing the free glucuronides. Reading at a wavelength of 5200 Å will give the indication of the total amount of conjugated glucuronides and free glucuronic acid which is present.

EXAMPLE VA

Test for Glucuronic Acid in Urine

To 10 cc of a urine sample 0.1 N ammonium hydroxide is added until a pH of 8 is reached. An excess of barium hydroxide is then added causing precipitation of the conjugated glucuronides. The sample is then centrifuged and the supernatant filtered. To 0.2 cc of the filtered supernatant is added 1.2 cc of sodium tetraborate in concentrated $H_2SO_4$. The mixture is mixed well in a test tube and chilled in crushed ice. The test tube is then heated for 5 minutes in boiling water and immediately cooled in ice until it becomes cold. Twenty microliters of 0.15% m-hydroxydiphenyl in 0.5% NaOH is then added. After waiting 5 minutes, the optical density is read at a wavelength of 5200 Å. The reading obtained represents the amount of free glucuronic acid present in the urine.

The relative amount of the total of conjugated glucuronides and free glucuronic acid which is present may be read in the same manner as set forth hereinabove in Example V.

EXAMPLE VI

Method of Administration of Glucuronide Therapy

After it has been determined that the patient has a tumor with β-glucuronidase activity, the first step of the treatment is to give him a dose of glucose as, for example, 100 g of honey, glucose or other sugar. Approximately 1 hour later, an intravenous drip is begun of a solution in distilled water containing approximately 10% glucose and 60 milli-equivalents sodium bicarbonate. Approximately 1 liter is administered, assuming no contraindications, and the pH of the urine is checked to determine that it has reached a pH of approximately 7.4. This will establish that the system has become alkalinized and it is now safe to administer the glucuronide. Another liter of the same glucose-bicarbonate solution, but also including the desired amount of glucuronide, is then administered. This is repeated daily as needed. When a glucuronide of a nitrile-containing cytotoxic aglycone is being used, immediately before, during or after administration of the glucuronide, 50 cc of a 25% solution of sodium thiosulfate is administered, preferably intravenously by slow drip. The sodium thiosulfate is preferably included in the glucose-bicarbonate-glucuronide solution which is being dripped intravenously. However, it may also be continued afterward for a greater margin of safety.

If there are contraindications for the administration of bicarbonate, then antacid may be orally administered. The important criterion is that the pH of the urine become approximately 7.4 and remain so during treatment.

The hyperacidification of the tumor cells is caused by a hyperglycemic condition in the patient. Therefore any hyperglycemic agent may be used as the hyperacidification agent, as for example, fructose, galactose, lactose or glucagon. Furthermore, it should be understood that this hyperglycemic condition may be effected in any known manner. For example, if the patient is diabetic then the condition can be brought about by decreasing the insulin administration.

Any agent which will raise the pH of the urine to approximately 7.4 can be used as the alkalinizing agent, including sodium or potassium bicarbonate or citrate, or other basic salts or antacids. While it is preferred that these be administered intravenously, they may be administered orally.

When the term "approximately 7.4" is used in the present specification and claims, with respect to the pH level to be maintained in the rest of the body, it should be understood that a pH level slightly above or below 7.4 may be used, although not preferred. As the pH decreases from 7.4 the β-glucuronidase activity increases (until the optimal pH is reached). Furthermore, below pH 7.0 the rest of the body will not be alkaline but will be acid. Above 7.4 the danger of alkalosis increases without any substantial further decrease in β-glucuronidase activity. A pH level of 7.4 is preferred as this is physiological pH and cannot be harmful to the body, and it is known that the β-glucuronidase activity in healthy organs is substantially nil at this pH level.

The dosage of the glucuronides should be monitored to avoid any side effects due to the massive release of toxins caused by the dying cancer cells. It may be preferable to to treat with glucuronides in short courses of several days, leaving several days in between, to allow any toxins released by the dying cancer cells to leave the body before the further treatment continues.

Besides intravenous administration, the glucuronides may be administered by any means of parenteral administration. However, the glucuronides should not be administered orally as it is known that β-glucuronidase is present in the digestive tract. The sodium thiosulfate, however, can be administered orally if a proper enteric coating is provided to avoid release in the stomach.

The amount of glucuronide to be administered to any given patient must be determined empirically and will differ depending on the condition of the patient. Relatively small amounts of glucuronide can be administered at first with steadily increasing daily dosages if no adverse effects are noted. Of course, the maximum safe toxicity dosage as determined in routine animal toxicity tests should never be exceeded.

It is clear that any tumor cells having β-glucuronidase activity may be treatable in accordance with the present invention with the remaining organs of the body being protected by the alkalinization step. Tumors which are known to have β-glucuronidase activity include solid breast tumors and their metastases, bronchogenic carcinoma and its metatases, and lymphomas. It is also known that neoplasms that do not have high β-glucuronidase activity, and therefore cannot be treated in accordance with the present invention, include leukemia. It must be understood, however, that this list is not meant to be complete, and that the prior art is aware of many other tumors that have β-glucuronidase activity. However, whether or not the art is presently aware that any given tumor has β-glucuronidase activity, this can be determined by any of the various methods of diagnosis discussed in the present specification and if it is determined that the tumor does have β-glucuronidase activity, the therapeutic treatment of the present invention can be effectively used.

When it is desired to induce hyperthermia to increase β-glucuronidase activity, a method should be selected by which the temperature is raised as much as possible without risking damage to healthy portions of the body, such as the eyes. An increase of about 2° C. for whole body hyperthermia and as much as 4.5° C. for local hyperthermia is preferred. The hyperthermia should be timed to last about an hour at the time of greatest glucuramide concentration at the tumor site. For example, when local microwave treatment is selected, it should begin about one half hour after commencement of the intravenous glucuronimide drip and be continued for about an hour. The proper dosage of known pyrogens to achieve the desired degree of hyperthermia would be known to those skilled in the art or could be easily empirically determined. A dosage of about 30 mg/day for dinitraphenol, for example, would be apt.

When estrogen or testosterone are to be administered, a dosage of 5-15 mg/body wt/day would provide the desired inducement of β-glucuronidase activity.

EXAMPLE VII

Method of Administration of Radioisotopes

If an aglycone labelled with a radioactive isotope is to be administered, the labelling may be accomplished by any method known per se. For diagnostic purposes only, relatively small amounts of these labelled glucuronides may be administered. They are otherwise administered in the same manner as set forth in Example VI for non-labelled glucuronides. Scanning of the body to determine whether any of the radio-labelled aglycone is retained by the body will indicate whether a tumor is present having β-gluduronidase activity and will also indicate where the tumor or any metastases thereof may be found. As noted above, gamma ray emitting isotopes, such as $^{131}I$, are particularly suitable for this purpose.

The radio-labelled glucuronides may also be used for in situ radiation therapy, particularly if an isotope is used having high beta-radiation activity, such as 133I. This will give the dual effect of attacking the cancer cells not only with the toxic aglycones but also with the beta-radiation. Again, the method of administration will be the same as set forth in Example VI.

Another utility for the present invention is the use of the boron-containing aglycone. It is already known that if boron atoms are bombarded with neutrons, they will break into lithium with the consequent release of positrons. If the boron atoms are attached to tumor tissue at the time, the positrons will be abruptly absorbed by the tumor tissue which will be lethal thereto. This process will have outstanding utility when the boron atoms are concentrated exclusively at the tumor cells in accordance with the process of the present invention.

EXAMPLE VIII

Method of Administration of pH Dependent Therapy

If the tumor cells are hyperacidified and the healthy tissue alkalinized in accordance with the method set forth in Example VI, an acid-alkaline pH differential will be created between the tumor cells and healthy cells. Thus, compounds whose activity or solubility is pH-dependent may be administered directly, without first conjugating with a glucuronide. Such compounds will selectively attack the acidified tumor cells without harming the remainder of the body which has an alkaline pH.

As in the method of Example VI, the patient is first given an oral dose of hyperglycaemic agent, such as 100 g of honey, glucose or other sugar. Approximately 1 hour later, an intravenous drip is begun of a solution in distilled water containing approximately 10% glucose and 60 milliequivalents sodium bicarbonate. Approximately 1 liter is administered, assuming no contraindications, and the pH of the urine is checked to determine that it has reached a pH of approximately 7.4. This will establish that the system has become alkalinized and it is now safe to administer the acid-active compound. Another liter of the same glucose-bicarbonate solution, but also including the desired amount of acid-active compound, is then administered. This is repeated daily as needed.

Compounds such as 2,4-dinitrophenol; 4,6-dinitro-o-cresol; 4-chloro-3,5-xylanol; chlorothymol; 2-phenyl-6-chlorophenol; 5-chloro-7-iodo-8-quinolinol and podophyllotoxin are all water soluble at alkaline pH's and lipid-soluble at acid pH's. Therefore, if the compounds are administered in the manner discussed above they will not create substantial harm to healthy tissue because they will be washed through the system relatively quickly. At the site of tumor tissue with acid pH, however, these compounds will come out of water solution and exert their cytotoxic or energy-supply effecting action on the tumor cells.

Compounds such as chloro-m-cresol, as well as 4,6-dinitro-o-cresol, 4-chloro-3,5-xylanol, chlorothymol and 2-phenyl-6-chlorophenol are more active at lower pH. Therefore, administration of these compounds with concomitant hyperacidification of the tumor cells and alkalinization of the remainder of the body will be even less harmful to healthy tissue, as their activity is diminished at the pH of the healthy tissue.

The dosage of the non-glucuronide compounds in accordance with this embodiment of the present invention will generally be somewhat less than the corresponding glucuronides as the glucuronide form of the compounds is substantially less toxic than the free compounds. The precise dosage must be determined empirically depending on the condition of the patient. Relatively small doses should be administered at first with steadily increasing daily dosage if no adverse effects are noted. Of course, the maximum safe toxicity dosage as determined in routine animal toxicity tests should never be exceeded.

Alternative acidifying and alkalinizing agents, as discussed hereinabove with respect to the glucuronide embodiment, may also be used with the present embodiment.

EXAMPLE IX

Method of Anti-Bacterial Administration

Glucuronide administration may be used in the treatment of bacterial infections if the bacteria involved are known to have $\beta$-glucuronidase activity. Examples of such bacteria are streptococci, staphylococci, and *E. coli*. The method of treatment of such bacterial infections will be similar to the method set forth in Example VI except that no hyperacidification will be necessary. This is so because bacterial $\beta$-glucuronidase is active at higher pH levels than $\beta$-glucuronidase of normal healthy internal organs. Furthermore, such a hyperacidification step would not affect the pH of the bacteria as its mechanism is specific to tumor cells.

The first step in antibacterial administration is an intravenous drip of distilled water and 60 milliequivalents sodium bicarbonate. Approximately one liter is administered and the pH of the urine is checked to determine that it has reached a pH of approximately 7.4. Another liter of the same bicarbonate solution, but also including the desired amount of glucuronide, is then administered in the same manner. This treatment may be repeated daily if necessary.

The alkalinizing agent may also be orally administered and any agent may be used that will alkalinize the body to an extent such that the pH of the urine becomes approximately 7.4. The glucuronide should not be administered orally but it may be administered by any means of parenteral administration.

Certain known anti-bacterial drugs having adverse side-effects may also be administered as glucuronides in accordance with the method of the present invention in order to reduce or eliminate these adverse effects. For example, chloroamphenicol is known to have a bone marrow depression effect which will not take place if the glucuronide is used. Neomycin is a known antibacterial which cannot be administered internally because of its toxicity. However, it can be orally administered for the treatment of infections of bacteria having high $\beta$-glucuronidase activity if first conjugated to glucuronic acid.

The radioisotope-labelled aglycone diagnostic procedure discussed hereinabove with respect to tumor diagnosis may also be used to determine the existance and location of bacterial infections. For example, a patient complaining of pain in the area of the appendix can receive the radiolabelled glucuronides. If no accumulation of isotope is found in the area then inflammation caused by bacteria with $\beta$-glucuronidase activity as a cause of the pain can be ruled out. In most instances inflammation in appendicitis is due to infection by bacteria with $\beta$-glucuronidase activity. Other use of such a diagnostic procedure would be obvious to those skilled in this art.

Besides the glucuronide compounds discussed hereinabove, any known conjugatable antibiotic may be conjugated with glucuronic acid for use against $\beta$-glucuronidase containing infections. This has the advantage of greatly diminishing the amount of free antibiotic circulating in the blood stream. The only antibiotic which is released will be released at the site of the infection. Therefore much smaller dosages may be given. Accordingly, the glucuronides of the present invention can serve as an internally administered local antibiotic. Because of the known $\beta$-glucuronidase activity in the digestion tract, no glucuronide should be administered orally, although any mode of parenteral administration is permissible.

If the antibiotic aglycone is known not to have any effect on the kidneys, then the alkalinization step can be eliminated. Many antibiotics, however, are known to be nephrotoxic to some extent and thus the alkalinization step is important to protect the kidneys.

EXAMPLE X

Biosynthesis of Mandelonitrile $\beta$-D-Glucuronic Acid

A 22 cc solution of 5% mandelonitrile (benzaldehyde cyanohydrin) in propylene-glycol is prepared and an intramuscular injection of this solution is given to a donkey or a goat. The 24 hr. urine is collected and acidified with acetic acid until the pH becomes 4. The urine is then filtered through a fiberglass filter and the filtrate is treated in any one of the following three different ways:

A. A saturated solution of lead acetate is added to the filtrate. The white precipitate that appears is separated by centrifuge and filtered. The filtrate is alkalined with $NH_3$ to pH 8 and then a saturated solution of basic lead acetate is added. The precipitate is washed with colder water and gaseous $H_2S$ is bubbled into it, the black precipitate of lead sulfide being separated. The filtrate is put into a vacuum until the volume is reduced to one third. A brown paste is achieved which is dissolved in absolute alcohol and kep overnight. The solution is filtered and the filtrate is vacuumized and ether added. The mandelonitrile $\beta$-D-glucuronic acid is crystallized from the ether solution.

B. The urine is acidified with hydrochloric acid to pH 4 and filtered through a fiberglass filter. Afterwards, the solution is dried in a vacuum state and the residue is dissolved in ether and recrystallized from the ether solution.

C. 0.1 N barium hydroxide water solution is added to the urine. The white precipitate of the barium salt of the mandelonitrile glucuronide is then washed in cold water and stirred and 0.1 N sulfuric acid is added. An insoluble solution of barium sulfate is removed and the supernatant vacuum dried and then recrystallized from ether solution.

Since mandelonitrile is very toxic and only a very small amount can be administered, the following semi-biosynthetic procedure may be used.

20 g mandelic amide (2-hydroxybenzamide) is mixed with goat or donkey food and the urine is collected for 24 hours. The mandelic amide glucuronide is separated by any of the methods described hereinabove. Acetic anhydride is then added and the glucuronide (2,3,4-triacetate glucopyranose mandelonitrile) is precipitated with barium hydroxide. The barium is removed with sulfuric acid and the glucuronide is recovered in vacuum as described hereinabove.

It will be obvious to those skilled in the art that various changes may be made without departing from the scope of the invention and the invention is not to be considered limited to what is described in the specification.

What is claimed is:

1. In a process of selectively delivering the aglycone of a glucuronide compound to tumor cells having higher $\beta$-glucuronidase activity than that of the surrounding tissues by hyperacidifying the tumor cells and then administering to the patient a glucuronide compound, the aglycone of which is to be delivered to the tumor cells, whereby the $\beta$-glucuronidase activity of the hyperacidified tumor cells causes deconjugation of the glucuronide compound at the site of the tumor cells and release of the aglycone thereat, the improvement wherein the tumor selectivity of the process is improved and the risk of deconjugation of the glucuronide compound at the site of non-tumor tissues is diminished, comprising:

administering to the patient an alkalinizing agent in an amount sufficient to maintain the pH level of the non-tumor tissues of the patient at approximately 7.4 during the glucuronide treatment.

2. Process in accordance with claim 1, wherein said compound is one in which the aglycone is toxic to tumor cells and exerts a higher toxic effect in an acid environment than in an alkaline environment or is water-soluble in an alkaline environment and water-insoluble or only poorly water-soluble in an acid environment.

3. Process in accordance with claim 2, wherein said glucuronide compound is selected from the group consisting of 2,4-dinitrophenol-$\beta$-D-glucuronic acid; 4-chloro-m-cresol-$\beta$-D-glucuronic acid; 4,6-dinitro-o-cresol-$\beta$-D-glucuronic acid; 4-chloro-3,5-xylanol-$\beta$-D-glucuronic acid; chlorothymol-$\beta$-D-glucuronic acid; 5-chloro-7-iodo-8-quinolinol-$\beta$-D-glucuronic acid; podophyllotoxin-$\beta$-D-glucuronic acid; 2-phenyl-6-chlorophenol-$\beta$-D-glucuronic acid; p-iodophenol $\beta$-D-glucuronic acid; and phenylsulfazole-$\beta$-D-glucuronic acid.

4. A process in accordance with claim 1, wherein said step of hyperacidifying the tumor cells comprises administering a hyperglycaemic agent in an amount sufficient to hyperacidify the tumor cells.

5. A process in accordance with claim 1, wherein said alkalinizing agent is administered orally or intravenously.

6. A process in accordance with claim 1, wherein said alkalinizing agent is administered prior to administration of said glucuronide compound, said glucuronide compound being administered after the pH of the urine of the patient is determined to be approximately 7.4 and wherein administration of said alkalinizing agent continues during administration of said glucuronide compound.

7. A process in accordance with claim 1 wherein the aglycone of said glucuranide compound is nitrile containing and further including the step of administering to the patient an amount of sodium thiosulfate sufficient to serve as antidote for cyanide poisoning.

8. A process in accordance with claim 1, further including the step of inducing hyperthermia at least at the site of the tumor being treated to an extent sufficient to substantially increase $\beta$-glucuronidase activity at the site without substantially affecting the overall health of the patient at least at the time of maximum glucuronide concentration at the tumor.

9. A process in accordance with claim 8, wherein said hyperthermia is induced locally at the tumor by administration of the glucuronide of a pyrogen, by microwave treatment or by passage of electrical current through the body.

10. A process in accordance with claim 1 further including the step of administering estrogen or testosterone substantially simultaneously with the administration of said glucuronide.

* * * * *